United States Patent
McGee et al.

(10) Patent No.: US 6,248,075 B1
(45) Date of Patent: *Jun. 19, 2001

(54) METHOD AND APPARATUS FOR FIXING THE ANATOMICAL ORIENTATION OF A DISPLAYED ULTRASOUND GENERATED IMAGE

(75) Inventors: David L. McGee, Sunnyvale; David K. Swanson, Mountain View, both of CA (US)

(73) Assignee: EP Technologies, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/507,053

(22) Filed: Feb. 21, 2000

Related U.S. Application Data (63) Continuation of application No. 08/938,406, filed on Sep. 26, 1997, now Pat. No. 6,027,451.

(51) Int. Cl.[7] .................................................. A61B 8/112
(52) U.S. Cl. ................................................ 600/463; 600/466
(58) Field of Search ..................................... 600/437, 439, 600/463, 466–467, 471, 424; 128/899, 916; 607/122

(56) References Cited

U.S. PATENT DOCUMENTS

| | | | |
|---|---|---|---|
| 5,000,185 | * 3/1991 | Yoch ..................................... | 600/466 |
| 5,002,059 | 3/1991 | Crowley et al. . | |
| 5,038,789 | 8/1991 | Frazin . | |
| 5,054,492 | * 10/1991 | Scribner et al. ...................... | 600/466 |
| 5,099,850 | 3/1992 | Matsui et al. . | |
| 5,131,397 | 7/1992 | Crowley . | |
| 5,307,816 | * 5/1994 | Hashimoto et al. .................. | 600/439 |
| 5,345,940 | 9/1994 | Seward et al. . | |
| 5,398,691 | 3/1995 | Martin et al. . | |
| 5,485,840 | * 1/1996 | Bauman .............................. | 600/439 |
| 5,485,845 | * 1/1996 | Verdonk et al. ...................... | 600/463 |
| 5,515,853 | 5/1996 | Smith et al. . | |
| 5,596,990 | * 1/1997 | Yoch et al. ........................... | 600/439 |
| 5,738,096 | 4/1998 | Ben-Haim . | |
| 5,797,849 | 8/1998 | Vesely et al. . | |
| 5,830,145 | 11/1998 | Tenhoff . | |
| 5,836,882 | 11/1998 | Frazin . | |
| 5,840,030 | * 11/1998 | Fereh-Petric et al. ................ | 600/439 |
| 5,840,031 | * 11/1998 | Crowley .............................. | 600/440 |
| 5,868,673 | 2/1999 | Vesely . | |
| 5,876,345 | * 3/1999 | Eaton et al. .......................... | 600/466 |
| 5,906,578 | * 5/1999 | Rajan et al. .......................... | 600/463 |
| 6,019,725 | * 2/2000 | Vesely et al. ........................ | 600/447 |
| 6,027,451 | * 2/2000 | McGee et al. ........................ | 600/463 |
| 6,095,976 | * 8/2000 | Nachtomy et al. .................. | 600/450 |

* cited by examiner

Primary Examiner—Francis J. Jaworski
(74) Attorney, Agent, or Firm—Henricks, Slavin & Holmes LLP (57) ABSTRACT

A diagnostic apparatus including a catheter carrying a first ultrasonic transducer adapted to be inserted into a patient, a second ultrasonic transducer adapted to be placed in spaced relation to the catheter at either a known location within the patient's body or a known location associated with the exterior surface of the patient's body, a processing device operably connected to at least the first ultrasonic transducer, and a display device.

26 Claims, 6 Drawing Sheets

METHOD AND APPARATUS FOR FIXING THE ANATOMICAL ORIENTATION OF A DISPLAYED ULTRASOUND GENERATED IMAGE

CROSS REFERENCE TO RELATED APPLICATIONS

This application is a continuation of application Ser. No. 08/938,406, filed Sep. 26, 1997 now U.S. Pat. No. 6,027,451.

BACKGROUND OF THE INVENTION

1. Field of Invention

The present invention relates generally to a device for diagnosing the body with ultrasonic waves and, more particularly, to an invasive ultrasound device.

2. Description of the Related Art

Non-invasive ultrasound techniques have been used for many years to produced detailed images of bodily structures. In a non-invasive procedure, a transducer is placed on the surface of the patient's body. An image is generated by producing an ultrasound signal with the transducer, receiving the reflected portion of the ultrasound signal with the transducer, and then transmitting a corresponding signal to a device which includes imaging circuitry and a display. In echocardiography, for example, a transducer is placed on the patient's chest and an image of the heart is produced.

In recent years, invasive ultrasound techniques have been developed. Here, a miniature ultrasound transducer is mounted on a catheter that is directed into the bodily structure of interest. The image shown on the display is a cross-section (or "slice") of that structure. One invasive ultrasound technique is intracardiac echocardiography. Here, a transducer is carried by a catheter into the patient's heart and the image shown on the display is a cross-section of the heart.

The inventor herein has determined that one disadvantage of conventional invasive ultrasound techniques is that the angular orientation of the displayed image is not fixed relative to an anatomical direction. Moreover, the image will often rotate as the transducer carrying catheter rotates relative to the patient. This rotation can be caused by operator handling of the catheter and the motion associated with cardiac and respiratory cycles. Despite the fact that physicians are familiar with the large scale anatomy of the heart and other organs, as well as the associated vascular structures, it is often difficult for them to place the displayed cross-sections within the context of the organ of interest. The physician must rely on his or her knowledge of bodily structures to first recognize the portion of the body being imaged. Once that task is completed, the physician must infer the rotational orientation of the image based on the typical orientation of that structure relative to the other portions of the patient's body.

SUMMARY OF THE INVENTION

Accordingly, the general object of the present invention is to provide a diagnostic method and apparatus which avoids, for practical purposes, the aforementioned problems. In particular, one object of the present invention is to provide a diagnostic method and apparatus which allows the physician to readily determine the anatomical orientation of the displayed image.

In order to accomplish at least some of these and other objectives, a diagnostic apparatus in accordance with one embodiment of the present invention includes a catheter carrying a first ultrasonic transducer adapted to be inserted into a patient, a second ultrasonic transducer adapted to be placed in spaced relation to the catheter at either a known location within the patient's body or a known location associated with the exterior surface of the patient's body, a processing device operably connected to at least the first ultrasonic transducer, and a display device. The first and second transducers each produce ultrasonic waves that will propagate through the adjacent bodily structure. The waves generated by the first transducer ultimately produce an image of the bodily structure of interest, while the waves generated by the second transducer establish a reference point.

The present invention provides a number of advantages over the prior art. For example, in accordance with one embodiment of the invention, the displayed image may include two portions—the first being representative of the bodily structure of interest and the second being be representative of the location of the second transducer. Because the location of the second transducer is a known location, such as anterior side of the patient, the displayed image will immediately convey the anatomical orientation of the image to the physician. In accordance with another embodiment of the invention, the displayed image may be automatically oriented in a predetermined anatomical orientation. For example, the image may be displayed such that the anterior side of the image is always at the top of the display. Here again, the displayed image will immediately convey the anatomical orientation of the image. Accordingly, the present invention solves the aforementioned problem in the art.

The present invention is particularly useful in intracardiac, intravascular and endoluminal imaging applications. The present invention may, however, be practiced in conjunction with imaging applications concerning other echogenic tissue, such as liver, parenchyma, bile duct, urinary bladder and intracranial tissue. In other words, the present invention may be practiced in any echogenic portion of the body that will allow passage of a catheter. Also, in addition to imaging, the present invention may also be practiced with a wide variety of therapeutic applications. For example, the imaging features of the present invention may be used to help physicians guide various catheter-based tools, such as ablation, laser, cutting and occluding tools, to their intended locations.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

DETAILED DESCRIPTION OF THE PREFERRED EMBODIMENTS

The following is a detailed description of the best presently known modes of carrying out the invention. This description is not to be taken in a limiting sense, but is made merely for the purpose of illustrating the general principles of the invention. The scope of the invention is defined by the appended claims.

Figure 1:
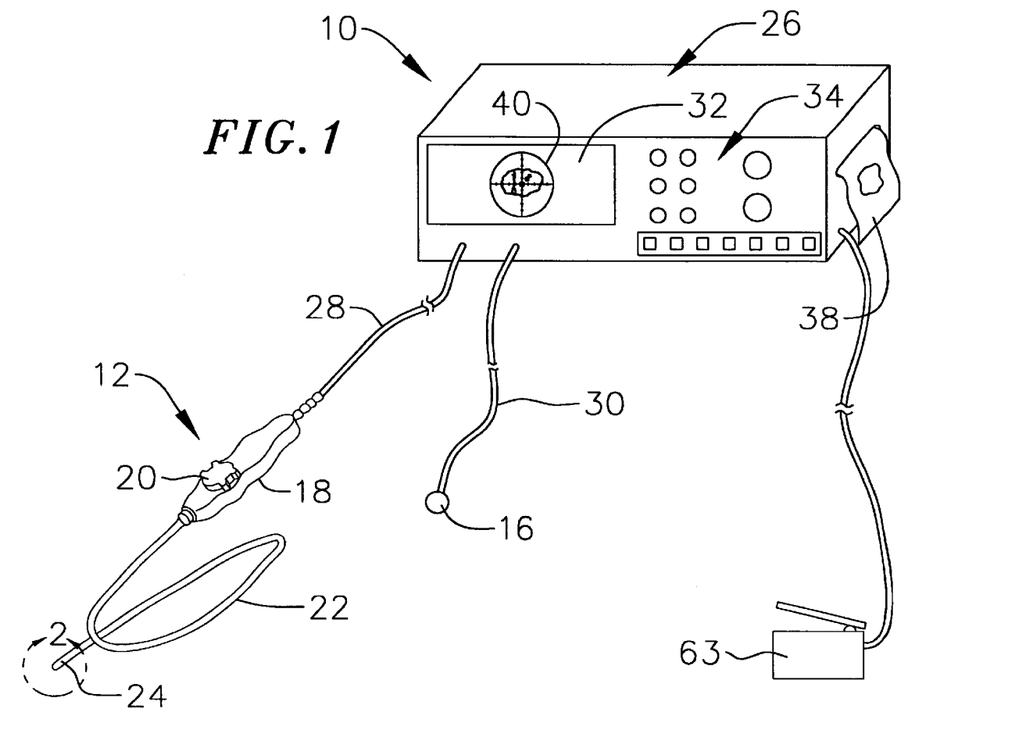
FIG. 1 is a perspective view of a diagnostic apparatus in accordance with a preferred embodiment of the present invention.
Figure 2:
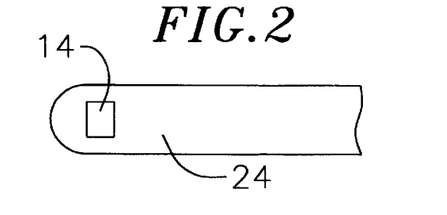
FIG. 2 is an enlarged view of a portion of the apparatus shown in FIG. 1.
Figure 3:
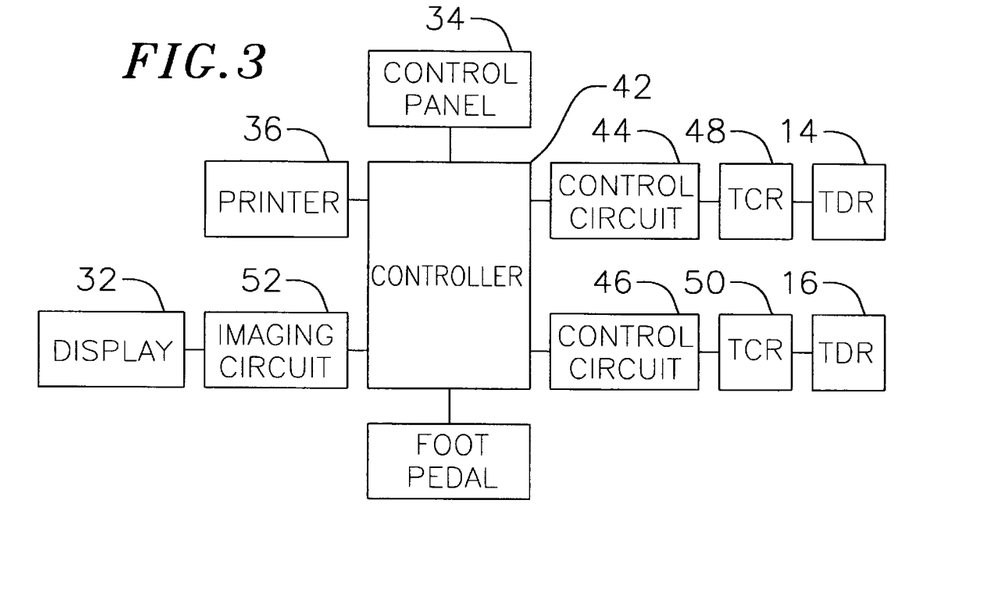
FIG. 3 is a block diagram of a diagnostic apparatus in accordance with the present invention.

As illustrated for example in FIGS. 1–3, a diagnostic apparatus 10 in accordance with a preferred embodiment of the present invention includes a catheter 12 having an ultrasonic transducer 14 associated therewith and an ultrasonic transducer 16 that may be secured to the exterior surface of the patient's body. The transducer 16, which acts a reference transducer, may instead be associated with a catheter so that it too may be inserted into the patient's body, or associated with a handle so that the physician can easily move the reference transducer 16 during examination. These aspects of the invention are discussed below with reference to FIGS. 9 and 11. The exemplary catheter 12 includes a handle 18, a steering knob 20, and a guide tube assembly 22. Such a catheter is disclosed in commonly assigned U.S. Pat. No. 5,456,664. The present invention may, however, be practiced with any catheter capable of positioning the transducer 14 at the desired location within the patient's body. The transducer 14 is located at the tip 24 of the guide tube assembly 22. With respect to the transducer itself, suitable ultrasonic transducers include, but are not limited to, phased array transducers, mechanical transducers, dynamic array transducers, offset stereoscopic imaging transducers, and multidimensional imaging transducers.

In the exemplary embodiment shown in FIGS. 1–3, the ultrasonic transducers 14 and 16 are connected to a control and display device 26 by electrical leads 28 and 30. The control and display device may be a unitary structure, as shown, or separated into independent control and display devices. The exemplary control and display device 26 includes a display 32, a control panel 34, and a printer 36 which may be used to produce a printed version 38 of the image 40 displayed on the display. The control and display device 26 also includes an electronic controller 42, such as a microprocessor-based controller, control circuits 44 and 46 which cause the transducers 14 and 16 to vibrate and produce ultrasound waves, and transceiver circuits 48 and 50 which receive and transmit signals via the electrical leads 28 and 30. The display 32 is driven by imaging circuitry 52.

Figure 4:
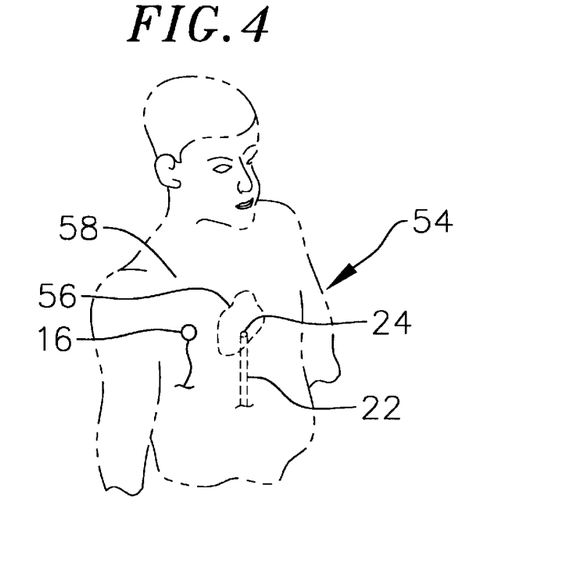
FIG. 4 is an illustration of an exemplary procedure which may be performed in accordance with the present invention.

One example of an imaging procedure in accordance with the present invention is illustrated in FIG. 4. Here, the catheter guide tube 22 is inserted into the patient 54 such that the transducer supporting tip 24 enters the patient's heart 56. The reference transducer 16 is secured to the patient's chest 58 (i.e. on the anterior portion of the patient's body) with adhesive tape or other suitable means. The catheter tip 24 and transducer 14 can, of course, be inserted into other portions of the patient's body and the reference transducer 16 repositioned accordingly.

During one mode of operation, the control and display device 26 causes transducers 14 and 16 to produce suitable ultrasonic waves that will propagate through the adjacent bodily structure. A portion of the waves (or signals) generated by the catheter-based transducer 14 will be reflected back from the bodily structure and impinge on the catheter-based transducer. The waves generated by the reference transducer 16 also impinge the catheter-based transducer 14. An electrical signal corresponding to the impinging waves is generated by the transducer 14 then and transmitted to the controller 42 via the transceiver circuit 48. A corresponding image is then generated by the imaging circuitry 52 and displayed on the display 32.

Figure 5:
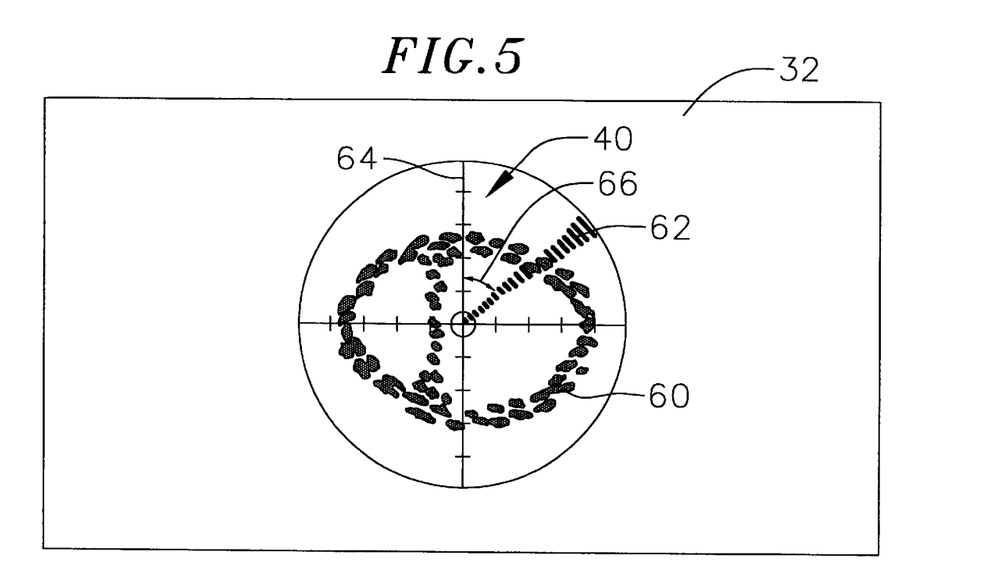
FIG. 5 is a plan view of a displayed image in accordance with one embodiment of the present invention.

As shown by way of example in FIG. 5, the image 40 presented on the display 32 has two significant portions. The first image portion 60 is a visual representation of a cross-section of the bodily structure of interest. In accordance with the exemplary procedure shown in FIG. 4, the first image portion 60 is a cross-section of the patient's heart. The second image portion 62 is indicative of the direction of the signals received by the catheter-based transducer 14 from the reference transducer 16. Because the reference transducer 16 is in a known location (here, the anterior side of the patient), the image 40 generated in accordance with the present invention will immediately convey its anatomical orientation to the reviewing physician.

The second image portion 62 may be continuously displayed, displayed intermittently, or displayed only upon demand. Continuous and intermittent display may be accomplished by simply supplying a continuous and intermittent signals to the reference transducer 16. On demand display may be provided through the use of a foot switch 63, a button on the control panel 34, or other suitable switching devices that allow the physician to selectively actuate the reference transducer 16.

Figure 6:
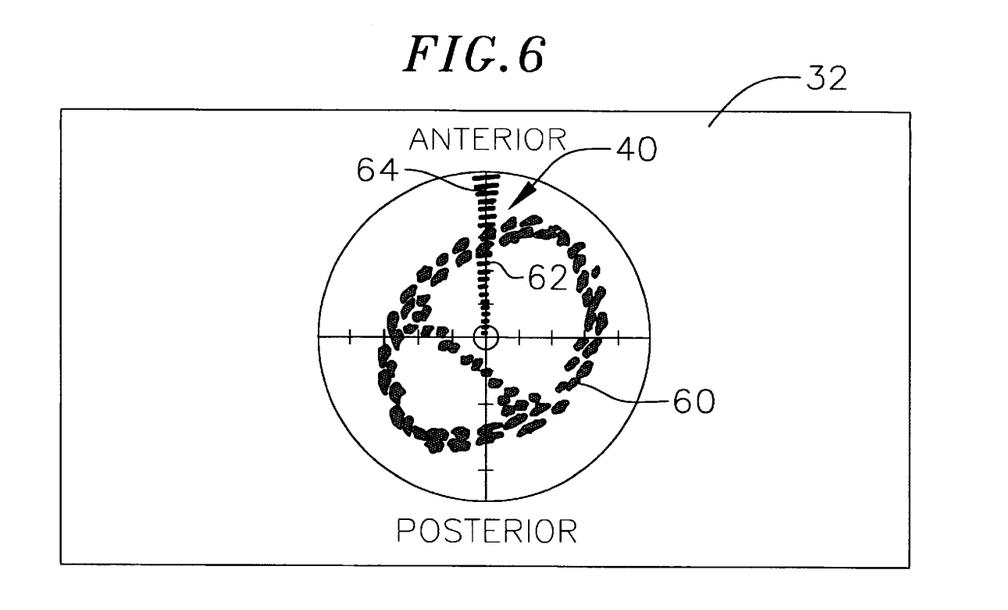
FIG. 6 is a plan view of a displayed image in accordance with another embodiment of the present invention.

The present invention may also be operated in various auto-orientation modes in which the image is displayed in a predetermined anatomical orientation. Referring more specifically to FIG. 6, the image 40 may be oriented such that the anterior portion of the patient's body is always at the top of the display 32. Such auto-orientation may be accomplished in a variety of manners. For example, the location of the reference transducer 16, i.e. anterior or posterior, and the desired orientation of the image 40 may be input into the controller 42 via the control panel 34. Once the controller has this information, the image may be analyzed and, if necessary, reoriented prior to display. The analysis is accomplished through conventional image analysis techniques performed by the imaging circuit 52 and controller 42.

In another embodiment of the invention, the second portion 62 of the image 40 (which corresponds to the reference transducer 16) will always be displayed on the same portion of the display, such as at the top portion, regardless of the anatomical location of the transducer.

Figure 7:
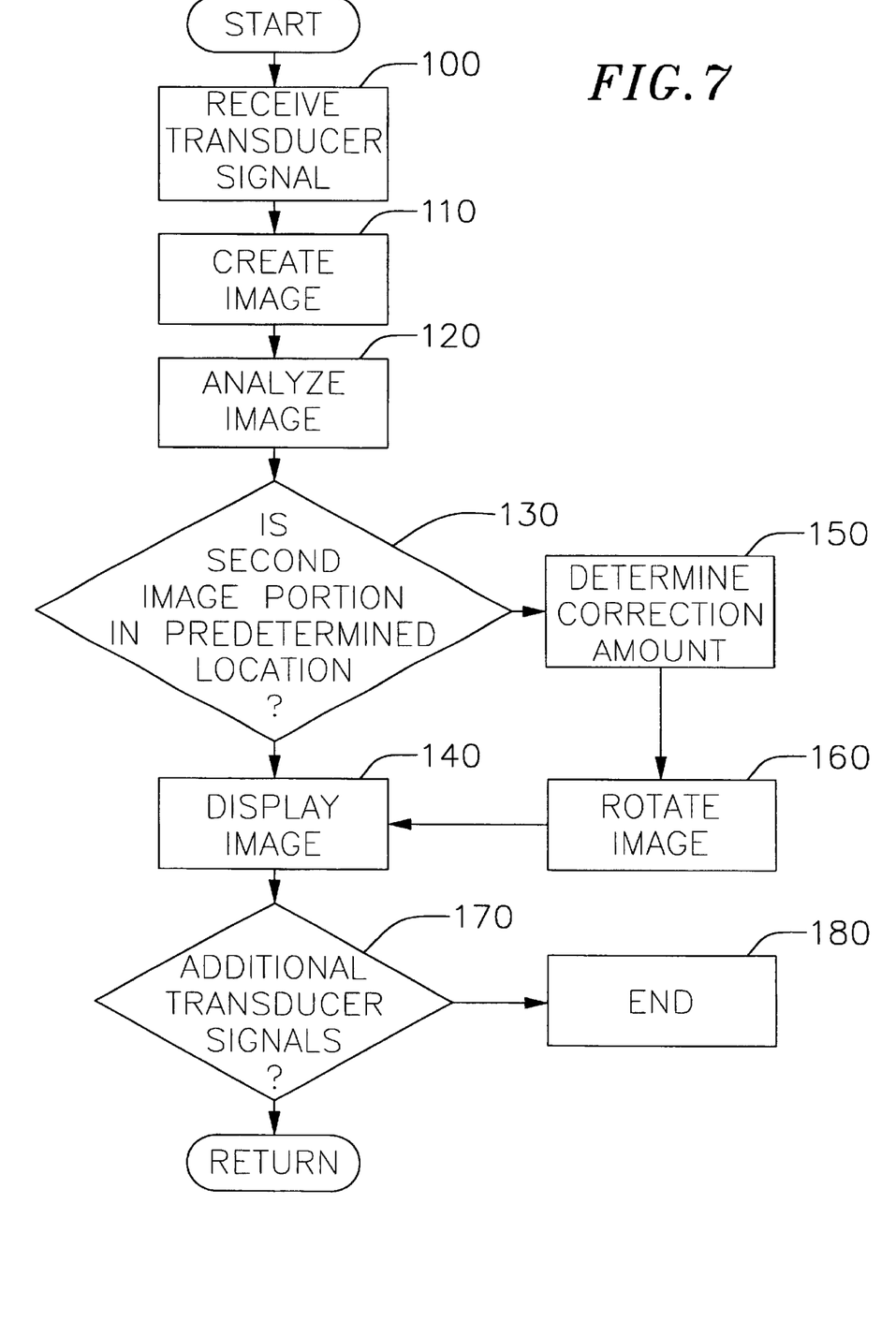
FIG. 7 is a flow chart in accordance with one embodiment of the present invention.

As shown by way of example in FIG. 7, a suitable program for performing the auto-orientation functions operates as follows. First, in steps 100–120, the signals from the catheter-based transducer 14 are received, an image is created by the imaging circuit 52 and, prior to display, the image is analyzed by controller 42. The step of analyzing the image consists primarily of isolating the second image portion 62 and determining its angular orientation. In step 130, the controller determines whether the second image portion 62 is oriented in a predetermined orientation. The predetermined orientation of the second image portion 62 is the orientation which corresponds to an image 40 displayed in the orientation desired by the physician or a preset orientation. For example, if the reference transducer 16 is placed on the anterior side of the patient and the desired image orientation is one where the anterior side is at the top of the display 32, then the predetermined orientation of the second image portion 62 would be one where the second image portion is aligned with the top portion of cross hair 64, as shown in FIG. 6. The image is then displayed on the display 32. [Step 140.]

Figure 8:
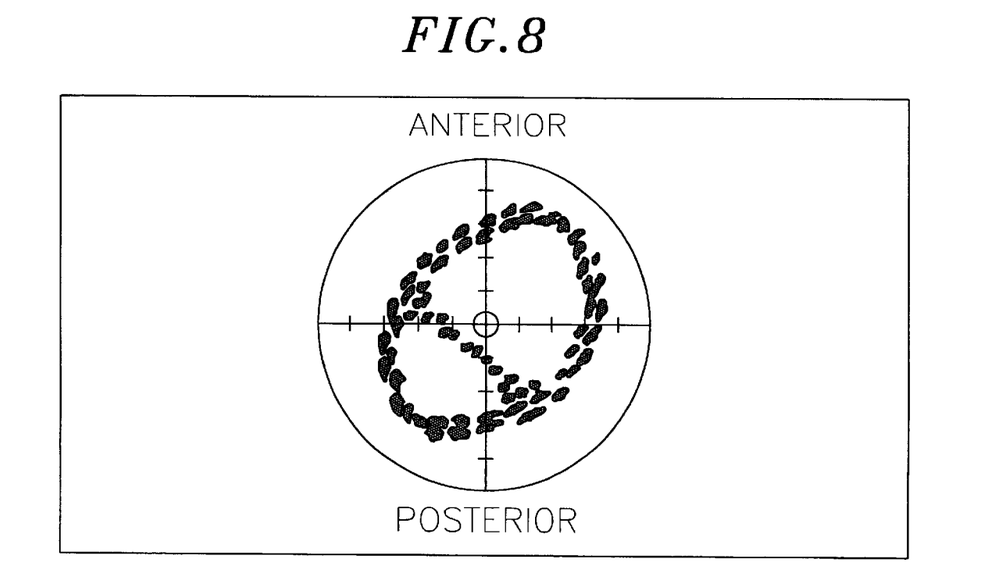
FIG. 8 is a plan view of a displayed image in accordance with another embodiment of the present invention.

When the second image portion 62 is not in the predetermined orientation, as is the case in FIG. 5, then an offset angle 66 (or correction amount) is calculated and the image 40 is rotated accordingly (steps 150 and 160) prior to display of the image. This process can, if desired, continue as long as signals are being received from the catheter-based transducer 14. [Steps 170 and 180.] As illustrated in FIG. 8, the second image portion 62, may be filtered out of the image 40 prior to display when the present invention is operating in an auto-orientation mode. Nevertheless, the automatic orientation of the image will continue as long as desired.

Figure 9:
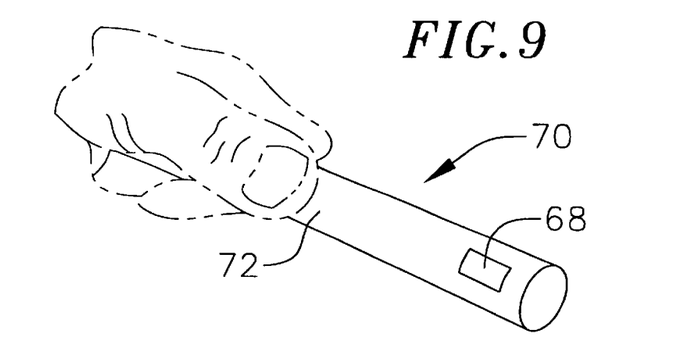
FIG. 9 is a perspective view of a hand held transducer-device.

In accordance with another exemplary embodiment of the present invention, and as shown by way of example in FIG. 9, a reference transducer 68 may be incorporated into a device 70 which has a handle 72. This allows the physician to move the reference transducer from one location to another during an examination when, for example, the patient has to be moved. The above-described auto-orientation features can, of course, be used to either reorient the image or maintain the image in the same orientation when the reference transducer is moved.

Figure 10:
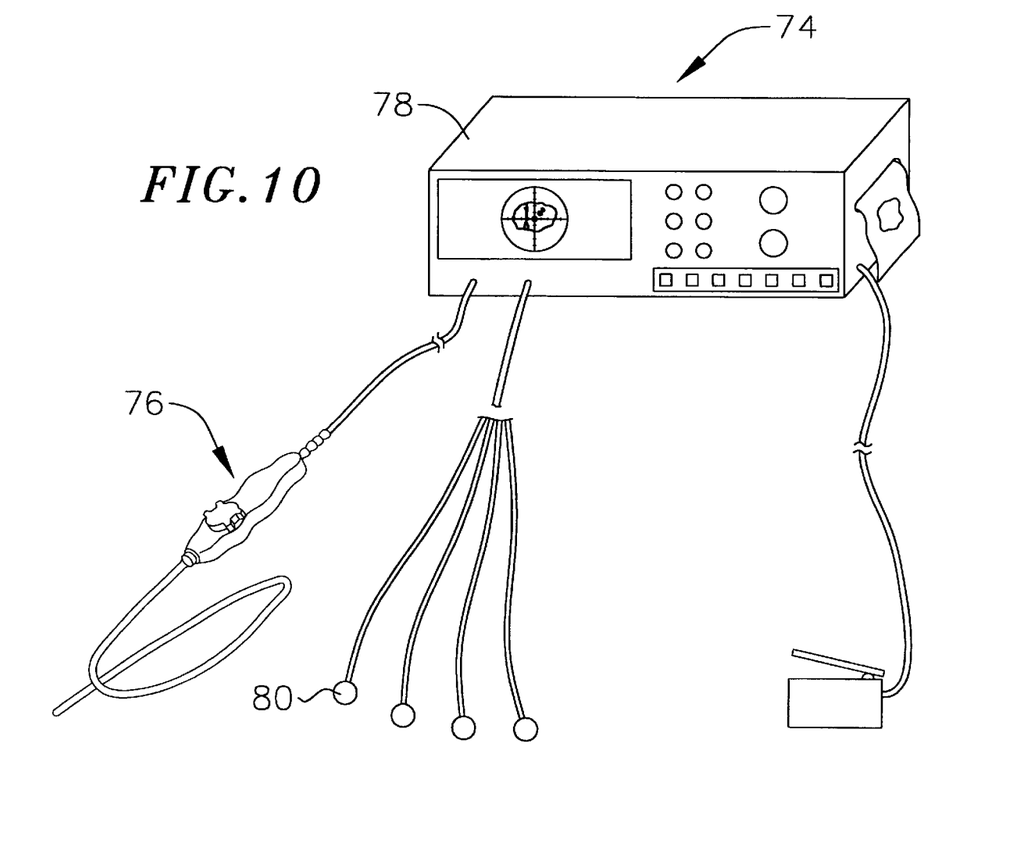
FIG. 10 a perspective view of a diagnostic apparatus in accordance with another preferred embodiment of the present invention.

Turning to FIG. 10, a diagnostic apparatus 74 in accordance with another preferred embodiment of the present invention includes a catheter 76 having an ultrasonic transducer associated therewith. The catheter-based transducer is electrically coupled to a display and control device 78 which operates in substantially the same manner as the display and control device 26 shown in FIG. 1. Here, however, a plurality of reference transducers 80 are provided. The reference transducers 80 may be positioned at different portions of the patient's body so as to provide a number of reference images similar to the image portion 62 shown in FIGS. 5 and 6. Alternatively, a switching device (such as a foot pedal or control knob) may be employed to allow the physician to selectively activate the reference transducers one at a time. Thus, the physician will be able switch between various known anatomical reference points.

Figure 11:
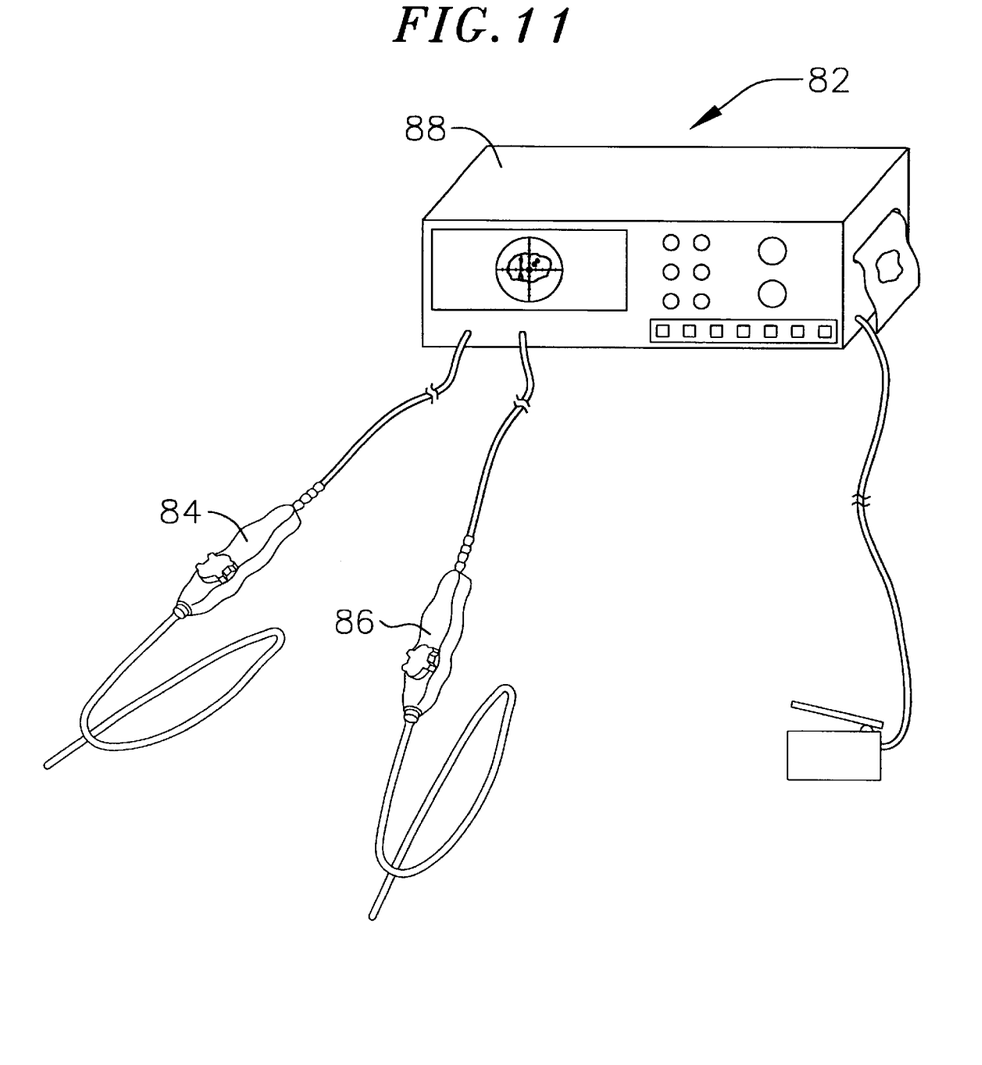
FIG. 11 a perspective view of a diagnostic apparatus in accordance with still another preferred embodiment of the present invention.

As shown by way of example in FIG. 11, a diagnostic apparatus 82 in accordance with another embodiment of the present invention includes a pair of catheters 84 and 86, each of which includes an ultrasound transducer. Both catheters are electrically coupled to a display and control device 88 which operates in substantially the same manner as the display and control device 26 shown in FIG. 1. The first catheter 86 functions as the imaging catheter. The transducer in the second catheter 86 acts as the reference transducer. Incorporating the reference transducer into a catheter allows the physician to place the anatomical reference point within the patient's body. The apparatus shown in FIG. 11 may, alternatively, include a plurality of reference catheters which will provide a plurality of reference points within the patient' body. Here too, a switching device may be employed so that the physician can selectively activate the reference transducers.

Although the present invention has been described in terms of the preferred embodiment above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

We claim:

1. A diagnostic apparatus for use with a patient having a body defining an exterior surface, the apparatus comprising:
    a catheter, carrying a first ultrasonic transducer for transmitting ultrasound and receiving resultant echoes, adapted to be inserted into the patient's body;
    a second ultrasonic transducer adapted to be placed in spaced relation to the catheter at one of a location within the patient's body and a location associated with the exterior surface of the patient's body;
    a display device for displaying an image corresponding to the echoes received by the first ultrasonic transducer and defining an angular orientation; and
    a processing device, operably connected to at least the first and second ultrasonic transducers, including means for comparing the angular orientation of the image to a predetermined angular orientation and means for reorienting the image.

2. An apparatus as claimed in claim 1, wherein the catheter defines a first catheter, the apparatus further comprising:
    a second catheter adapted to be inserted into the patient's body, the second catheter carrying the second ultrasonic transducer.

3. An apparatus as claimed in claim 1, wherein the second ultrasonic transducer comprises a plurality of second ultrasonic transducers.

4. An apparatus as claimed in claim 1, wherein the second ultrasonic transducer comprises a hand-held ultrasonic transducer.

5. An apparatus as claimed in claim 1, further comprising:
    an ultrasonic energy source operably connected to the second ultrasonic transducer.

6. An apparatus as claimed in claim 5, further comprising:
    a manually operable switch operably connected to the ultrasonic energy source.

7. An apparatus as claimed in claim 5, wherein the ultrasonic energy source supplies ultrasonic energy at a substantially constant rate.

8. An apparatus as claimed in claim 5, wherein the ultrasonic energy source supplies ultrasonic energy intermittently.

9. An apparatus as claimed in claim 1, further comprising:
    a position indicator displayed by the display device, the position indicator being indicative of a location of the second ultrasonic transducer relative to the first ultrasonic transducer.

10. A diagnostic method for use with a patient having a body defining an exterior surface, comprising the steps of:
    inserting a catheter, carrying a first ultrasonic transducer, into the patient's body;
    positioning a second ultrasonic transducer in spaced relation to the catheter at one of a location within the patient's body and a location associated with the exterior surface of the patient's body;

transmitting first ultrasound signals with the first ultrasonic transducer and receiving resultant echoes of the first ultrasound signals with the first ultrasonic transducer;

transmitting second ultrasound signals with the second ultrasonic transducer and receiving the second ultrasound signals with the first ultrasonic transducer;

generating an image corresponding to at least the echoes of the first ultrasound signals received by the first ultrasonic transducer, the image defining and image orientation;

comparing the image orientation to a predetermined image orientation;

reorienting the image if the image orientation does not correspond to the predetermined image orientation; and displaying the image.

11. A method as claimed in claim 10, further comprising the step of:

displaying an image corresponding to the second ultrasound signals received by the first ultrasonic transducer.

12. A method as claimed in claim 10, further comprising the steps of:

moving the second ultrasonic transducer to one of a second location within the patient's body and a second location associated with the exterior surface of the patient's body;

transmitting additional first ultrasound signals with the first ultrasonic transducer and receiving resultant echoes of the additional first ultrasound signals with the first ultrasonic transducer; and transmitting additional second ultrasound signals with the second ultrasonic transducer and receiving the additional second ultrasound signals with the first ultrasonic transducer.

13. A method as claimed in claim 10, wherein the step of positioning a second ultrasonic transducer in spaced relation to the catheter comprises positioning the second ultrasonic transducer on the exterior surface of the patient's body.

14. A method as claimed in claim 10, wherein the step of positioning a second ultrasonic transducer in spaced relation to the catheter comprises inserting a second catheter, carrying the second ultrasonic transducer, into the patient's body.

15. A method as claimed in claim 10, wherein the second ultrasonic transducer comprises a plurality of second ultrasonic transducers and the step of positioning a second ultrasonic transducer in spaced relation to the catheter comprises positioning second ultrasonic transducers in spaced relation to one another and to the catheter.

16. A method as claimed in claim 10, wherein the step of inserting the catheter into the patient's body comprises inserting the catheter into the patient's heart.

17. A method as claimed in claim 10, further comprising the step of:

displaying an anatomical orientation indicator.

18. A diagnostic apparatus for use with a patient having a body defining an exterior surface, the apparatus comprising:

a catheter, carrying a first ultrasonic transducer for transmitting ultrasound and receiving resultant echoes, adapted to be inserted into the patient's body;

a second ultrasonic transducer adapted to be placed in spaced relation to the catheter at one of a location within the patient's body and a location associated with the exterior surface of the patient's body;

a display device for displaying an image corresponding to the echoes received by the first ultrasonic transducer and defining an angular orientation; and a processing device, operably connected to at least the first and second ultrasonic transducers, that compares the angular orientation of the image to a predetermined angular orientation and reorients the image based on the comparison.

19. An apparatus as claimed in claim 18, wherein the catheter defines a first catheter, the apparatus further comprising:

a second catheter adapted to be inserted into the patient's body, the second catheter carrying the second ultrasonic transducer.

20. An apparatus as claimed in claim 18, wherein the second ultrasonic transducer comprises a plurality of second ultrasonic transducers.

21. An apparatus as claimed in claim 18, wherein the second ultrasonic transducer comprises a hand-held ultrasonic transducer.

22. An apparatus as claimed in claim 18, further comprising:

an ultrasonic energy source operably connected to the second ultrasonic transducer.

23. An apparatus as claimed in claim 22, further comprising:

a manually operable switch operably connected to the ultrasonic energy source.

24. An apparatus as claimed in claim 22, wherein the ultrasonic energy source supplies ultrasonic energy at a substantially constant rate.

25. An apparatus as claimed in claim 22, wherein the ultrasonic energy source supplies ultrasonic energy intermittently.

26. An apparatus as claimed in claim 18, further comprising:

a position indicator displayed by the display device, the position indicator being indicative of a location of the second ultrasonic transducer relative to the first ultrasonic transducer.

* * * * *